United States Patent
Caruel et al.

(10) Patent No.: US 10,829,469 B2
(45) Date of Patent: Nov. 10, 2020

(54) CONFIGURATIONAL STEREOISOMER OF DIFETHIALONE, COMPOSITION AND RODENTICIDE BAIT COMPRISING SAME, AND METHOD FOR CONTROLLING TARGET RODENT PESTS

(71) Applicants: LIPHATECH, Pont-du-Casse (FR); INSTITUT ENSEIGNEMENT SUPERIEUR ET RECHERCHE EN ALIMENTATION SANTE ANIMALE SCIENCES AGRONOMIQUE, Marcy l'etoile (FR)

(72) Inventors: Hervé Caruel, Moncaut (FR); Etienne Benoit, Lyons (FR); Isabelle Fourel, Miribel (FR); Virginie Lattard, Lyons (FR)

(73) Assignees: LIPHATECH, Pont-du-Casse (FR); INSTITUT ENSEIGNEMENT SUPERIEUR ET RECHERCHE EN ALIMENTATION SANTE ANIMALE SCIENCES AGRONOMIQUE, Marcy l'etoile (FR)

( * ) Notice: Subject to any disclaimer, the term of this patent is extended or adjusted under 35 U.S.C. 154(b) by 0 days.

(21) Appl. No.: 16/061,117

(22) PCT Filed: Dec. 6, 2016

(86) PCT No.: PCT/EP2016/079855
§ 371 (c)(1),
(2) Date: Sep. 10, 2018

(87) PCT Pub. No.: WO2017/097745
PCT Pub. Date: Jun. 15, 2017

(65) Prior Publication Data
US 2019/0016697 A1    Jan. 17, 2019

(30) Foreign Application Priority Data

Dec. 11, 2015 (FR) .................................... 15 62225

(51) Int. Cl.
*C07D 335/06* (2006.01)
*A01N 25/00* (2006.01)
*A01N 43/18* (2006.01)
*B01D 15/38* (2006.01)
*C07B 57/00* (2006.01)

(52) U.S. Cl.
CPC .......... *C07D 335/06* (2013.01); *A01N 25/004* (2013.01); *A01N 43/18* (2013.01); *B01D 15/3833* (2013.01); *C07B 57/00* (2013.01); *C07B 2200/07* (2013.01)

(58) Field of Classification Search
CPC ...... C07D 335/06; A01N 43/18; A01N 25/00; B01D 15/38
See application file for complete search history.

(56) References Cited

U.S. PATENT DOCUMENTS

| 4,585,786 A | 4/1986 | Berthelon |
| 4,783,481 A | 11/1988 | Swaine |
| 2005/0181003 A1 | 8/2005 | Endepols et al. |

FOREIGN PATENT DOCUMENTS

| EP | 0 147 052 A2 | 7/1985 |
| EP | 0 161 163 A1 | 11/1985 |
| EP | 2 090 164 A1 | 8/2009 |
| WO | 2015/189320 A1 | 12/2015 |

OTHER PUBLICATIONS

Koubek et al., "High pressure liquid chromatographic determination of the rodenticide brodifacoum in rat tissue", Journal of the Association of Official Analytical Chemists, 1979, pp. 1297-1301, vol. 62, No. 6.
International Search Report, dated Jan. 23, 2017, from corresponding PCT application No. PCT/EP2016/079855.

*Primary Examiner* — Zohreh A Fay
(74) *Attorney, Agent, or Firm* — Ipsilon USA, LLP

(57) ABSTRACT

Disclosed is a laevorotatory enantiomer of the configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration.

8 Claims, 5 Drawing Sheets

CONFIGURATIONAL STEREOISOMER OF DIFETHIALONE, COMPOSITION AND RODENTICIDE BAIT COMPRISING SAME, AND METHOD FOR CONTROLLING TARGET RODENT PESTS

The invention relates to a configurational stereoisomer of difethialone as an isolated compound, to a composition and a rodenticidal bait comprising such a configurational stereoisomer and to a process for controlling target rodent pests. The invention thus relates to the technical field of controlling populations of target rodent pests.

It is known practice to use rodenticidal baits as poisons for target rodent pests. It is known from EP 2 090 164 that difethialone is a second-generation anticoagulant acting in a single dose. US 2005/181003 describes a rodenticidal bait in gel form comprising difethialone in a mass proportion of 25 ppm.

The baits of EP 2 090 164 and US 2005/181003 are liable to be consumed by animals other than target rodent pests when they are made available to target rodent pests. They may be consumed directly (primary consumption) by domestic animals or pets. They may also be consumed accidentally by humans. Such consumption may result in poisoning, which may be lethal, of these domestic animals or pets or of humans.

In addition, a fraction of the difethialone of these rodenticidal baits may be ingested (secondary consumption) by animals—especially by birds—which prey on weakened rodent pests that have consumed such a rodenticidal bait, or by animals which carrion-feed on rodent pests that have died from having consumed such a rodenticidal bait. This secondary consumption is liable in the long term to result in the death of these predatory or carrion-feeding animals, which may be animals—especially birds—belonging to protected species.

The invention is thus directed towards overcoming these drawbacks by proposing a configurational stereoisomer of difethialone, a composition and a rodenticidal bait comprising such a configurational stereoisomer and a process for controlling target rodent pests, which are not only effective for controlling the populations of target rodent pests but also limit the risks of poisoning of non-target animals—especially domestic or reared animals, pets or humans—which accidentally consume such a rodenticidal bait, and also the risks of poisoning, named secondary poisoning, of wild animals—for example foxes or birds—which prey on weakened target rodent pests which have consumed the rodenticidal bait or of wild animals which carrion-feed on target rodent pests that have died from being poisoned.

The invention is also directed towards proposing a configurational stereoisomer of difethialone, a composition and a rodenticidal bait comprising such a configurational stereoisomer and a process for controlling target rodent pests, the use of which complies with the rules of environmental protection, especially with respect to the protection of birds, and in particular birds of prey.

The invention is also directed towards proposing a configurational stereoisomer of difethialone, a composition and a rodenticidal bait comprising such a configurational stereoisomer and a process for controlling target rodent pests, which do not require, in order to control a population of target rodent pests, the use of massive doses of a rodenticidal agent and which are friendly towards the environment and the health of humans and non-target animals—especially birds.

The invention is also directed towards proposing a configurational stereoisomer of difethialone, a composition and a rodenticidal bait comprising such a configurational stereoisomer and a process for controlling target rodent pests, which are able to be used for controlling target rodent pests that are resistant to known baits for controlling target rodent pests.

The invention is thus also directed towards proposing an alternative to known rodenticidal baits.

To do this, the invention relates to a laevorotatory enantiomer of a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration.

Throughout the text:
the term "difethialone" denotes the compound 3-(4'-bromobiphenyl-4-yl)-1-(4-hydroxythiocoumarin-3-yl)-1,2,3,4-tetrahydronaphthalene or 3-[3-[4-(4-bromophenyl)phenyl]-1-tetralinyl]-2-hydroxy-4-thiochromenone or 3-[3-(4'-bromo[1,1'-biphenyl]-4-yl)-1,2,3,4-tetrahydro-1-naphthalenyl]-4-hydroxy-2H-1-benzothiopyran-2-one of formula (I) below:

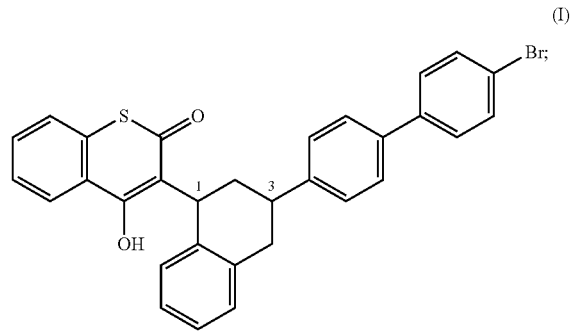 [SMILES: O=c1sc2ccccc2c(O)c1C1CC(c2ccc(-c3ccc(Br)cc3)cc2)Cc2ccccc21]

in which are indicated the numbers of carbons 1 and 3 of the 1,2,3,4-tetrahydronaphthalene group;

the term "stereoisomers" denotes isomers of the same semi-structural formula, but in which the relative position of the atoms differs in space. The term "configurational stereoisomers" denotes stereoisomers for which conversion from one to the other of these configurational stereoisomers requires the cleavage/reformation of an interatomic covalent bond. Thus, the term "configurational stereoisomers" denotes stereoisomers which are not conformational isomers (or "rotamers", for which conversion from one to the other of the conformational isomers is accompanied only by rotation of a part of the molecule about the axis of a σ (sigma) bond formed by axial orbital overlap);

the term "homo-stereoisomer" of difethialone denotes the configurational stereoisomer of difethialone of formula 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration (1S,3S or 1R,3R), said absolute configurations being determined according to the sequential priority rules and the Cahn-Ingold-Prelog (CIP) nomenclature;

the term "hetero-stereoisomer" of difethialone denotes the configurational stereoisomer of difethialone of formula 3-(4'-bromobiphenyl-4-yl-1-(4-hydroxythiocoumarin- 3-yl)-1,2,3,4-tetrahydronaphthalene, in which carbons 1 and 3 of the 1,2,3,4-tetrahydronaphthalene group have different absolute configurations (1S,3R or 1R,3S), said absolute configurations being determined according to the sequential priority rules and the Cahn-Ingold-Prelog (CIP) nomenclature;

the term "amount" means a molar amount, a mass amount or a volume amount. The proportions are thus proportions of a molar amount relative to a molar amount, of a mass amount relative to a mass amount, or of a volume amount relative to a volume amount;

the term "substantially" indicates, in the usual manner, that a structural or functional characteristic should not be taken as marking an abrupt discontinuity, which would have no physical meaning, but covers not only this structure or this function, but also slight variations of this structure or of this function which produce, in the technical context under consideration, an effect of the same nature, or else of the same degree;

the expressions "high-pressure liquid chromatography" or "high-performance liquid chromatography" (HPLC) denote "HPLC" chromatography or "High Performance Liquid Chromatography"; and the term "retention time" denotes the time, measured at the top of the peak in the chromatogram, for which a compound is retained on a chromatography column.

The invention thus relates to the laevorotatory enantiomer of said homo-stereoisomer of difethialone in isolated form. The invention relates to the laevorotatory enantiomer of said homo-stereoisomer of difethialone in a form separated from the dextrorotatory enantiomer of said homo-stereoisomer of difethialone and from the dextrorotatory and laevorotatory enantiomers of a configurational stereoisomer of difethialone, named "hetero-stereoisomer", in which carbons 1 and 3 of the 1,2,3,4-tetrahydronaphthalene group have different absolute configurations.

The inventors have discovered that it is possible to separate the laevorotatory and dextrorotatory enantiomers of said homo-stereoisomer of difethialone and of said hetero-stereoisomer of difethialone by high-pressure liquid chromatography in isocratic mode and under particular conditions by using a chromatography column comprising a chiral stationary phase. Specifically, it was not known at the date of the invention how to separate the laevorotatory enantiomer of said homo-stereoisomer of difethialone and the dextrorotatory enantiomer of said homo-stereoisomer of difethialone.

The inventors succeeded in performing this separation by choosing a particular HPLC chromatography column, LUX® Cellulose-3 (Phenomenex, Le Pecq, France) of dimensions 150×2 mm and comprising a chiral stationary phase constituted of porous particles of cellulose tris(4-methylbenzoate), having a particle size of 3 µm and a porosity of 1000 Å. They used, as mobile phase, an eluent formed from a mixture of acetonitrile (A) and water comprising formic acid in a volume proportion of 0.1% in water (B) with an A/B volume ratio of 80/20. The flow rate of the mobile phase in the column is kept at a value of 0.25 mL/minute and the separation is performed at room temperature. The concentration of the composition to be analysed is 1 µg of difethialone per millilitre of acetonitrile and the volume injected onto the column is 1 µL. Detection may be performed by tandem mass spectrometry (MS/MS). Detection may also be performed by photometry or by spectrophotometry by adjusting the difethialone concentration and the injection volume for the purpose of obtaining optimum detection and by measuring the value of the area under the peak for each enantiomer.

Under these experimental conditions, the value of the retention time ($t_1$) for the laevorotatory enantiomer of said homo-stereoisomer according to the invention may vary depending on the operating conditions—especially depending on the column temperature conditions—and may be between 7.8 minutes and 8.2 minutes. The value of the retention time ($t_4$) for the dextrorotatory enantiomer of said homo-stereoisomer may vary depending on the operating conditions—especially depending on the column temperature conditions—and may be between 14.0 minutes and 14.4 minutes, such that the dextrorotatory and laevorotatory enantiomers of said homo-stereoisomer may be separated by high-pressure liquid chromatography on a chiral column.

Under these same experimental conditions, the value of the retention time ($t_3$) for the dextrorotatory enantiomer of said hetero-stereoisomer of difethialone may vary depending on the operating conditions—especially depending on the column temperature conditions—and may be between 11.3 minutes and 11.8 minutes. The value of the retention time ($t_2$) for the laevorotatory enantiomer of said hetero-stereoisomer of difethialone may vary depending on the operating conditions—especially depending on the column temperature conditions—and may be between 9.0 minutes and 9.5 minutes.

Thus, under these experimental conditions, the order of elution of the configurational stereoisomers of difethialone is such that $t_1<t_2<t_3<t_4$. The retention time values $t_1$, $t_2$, $t_3$ and $t_4$ are liable to vary, especially with the temperature of the chromatography column. However, under these chromatographic conditions, the order of elution of the configurational stereoisomers of difethialone remains unchanged.

The invention thus relates to the laevorotatory enantiomer of said homo-stereoisomer of difethialone in isolated form and having the property of being able to be eluted, under the chromatography conditions described above, first from among the four configurational stereoisomers of difethialone.

The laevorotatory enantiomer of said homo-stereoisomer of difethialone isolated in pure form according to the invention, dissolved in methanol at a concentration of 0.81 g/L and placed in a quartz spectrophotometry cuvette, has a circular dichroism spectrum acquired at 25° C. with negative circular dichroism values between 210 nm and 320 nm.

The laevorotatory enantiomer of said homo-stereoisomer of difethialone isolated in pure form according to the invention, dissolved in chloroform ($CHCl_3$), has a specific optical rotation $[\alpha]^{25\ °C}_{589\ nm}$, measured at 25° C. and on the sodium D line (589 nm), having a value of −14.8°.

The laevorotatory enantiomer of said homo-stereoisomer of difethialone isolated in pure form according to the invention has, on proton magnetic resonance ($^1H$-NMR) spectroscopy at 500 MHz in $CDCl_3$, a multiplet with a chemical shift (δ) of between 4.9 ppm and 5.1 ppm corresponding to the proton borne by carbon 1 of the 1,2,3,4-tetrahydronaphthalene group of said homo-stereoisomer of difethialone.

Said hetero-stereoisomer of difethialone and said homo-stereoisomer of difethialone are distinguished by their proton NMR spectra. In the proton NMR spectrum acquired in $CDCl_3$, the chemical shift of the proton borne by carbon 1 of the 1,2,3,4-tetrahydronaphthalene group of said hetero-stereoisomer of difethialone is between 5.2 ppm and 5.4 ppm, especially about 5.3 ppm.

The invention also relates to a composition comprising the laevorotatory enantiomer according to the invention, with the exclusion of a racemic mixture of laevorotatory and dextrorotatory enantiomers of said homo-stereoisomer of difethialone, i.e. with the exclusion of a composition in which the laevorotatory enantiomer of said homo-stereoisomer of difethialone is in optically inactive mixture with the dextrorotatory enantiomer of said homo-stereoisomer of difethialone.

The invention thus also relates to a composition comprising the laevorotatory enantiomer of the configurational stereoisomer of difethialone, named homo-stereoisomer, of formula 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration, with the exclusion of a mixture in which the laevorotatory enantiomer and the dextrorotatory enantiomer of said homo-stereoisomer of difethialone are in equal amounts. The invention thus relates to such a composition in which the laevorotatory enantiomer and the dextrorotatory enantiomer of said homo-stereoisomer of difethialone are in different amounts.

Advantageously and according to the invention, said homo-stereoisomer is predominantly in laevorotatory enantiomer form. Advantageously, a composition according to the invention comprises said homo-stereoisomer of difethialone predominantly in laevorotatory enantiomer form.

Throughout the text, the term "said homo-stereoisomer is predominantly in laevorotatory enantiomer form" means that the (mass, molar or volume) amount of laevorotatory enantiomer of said homo-stereoisomer of difethialone is in major amount—greater than 50%—in the total amount of said homo-stereoisomer of difethialone present in the composition (in all its dextrorotatory and laevorotatory enantiomer forms).

Advantageously and according to the invention, the composition comprises an amount of the laevorotatory enantiomer of said homo-stereoisomer of difethialone such that the ratio of this amount to the amount of said homo-stereoisomer of difethialone in the composition is greater than 50%, especially greater than 60%, in particular greater than 70%, more particularly greater than 80%, preferably greater than 90%, more preferentially greater than 95%, particularly preferentially greater than 98%, even more preferentially greater than 99% or about 100%. Advantageously, the composition comprises an amount of the laevorotatory enantiomer of said homo-stereoisomer of difethialone such that the ratio of this amount to the amount of said homo-stereoisomer of difethialone in the composition is greater than 75%, preferably between 85% and 100%, more preferentially between 90% and 99%. Advantageously, the composition comprises an amount of the laevorotatory enantiomer of said homo-stereoisomer of difethialone such that the ratio of this amount to the amount of said homo-stereoisomer of difethialone is between 96% and 100%.

In a composition according to the invention:
the amount of laevorotatory enantiomer of said homo-stereoisomer of difethialone relative to the sum of the amounts of each of the (laevorotatory and dextrorotatory) enantiomers of said homo-stereoisomer of difethialone is greater than 0.5 (greater than 50%);
the concentration of laevorotatory enantiomer of said homo-stereoisomer of difethialone relative to the sum of the concentrations of each of the (laevorotatory and dextrorotatory) enantiomers of said homo-stereoisomer of difethialone is greater than 0.5 (greater than 50%); and
the proportion of laevorotatory enantiomer of said homo-stereoisomer of difethialone in the composition is greater than the proportion of the other (dextrorotatory) enantiomer of said homo-stereoisomer of difethialone. In a composition according to the invention, the proportion of laevorotatory enantiomer of said homo-stereoisomer of difethialone in the composition is more than 50% relative to said homo-stereoisomer of difethialone.

Advantageously, the composition may comprise a proportion of dextrorotatory enantiomer of said homo-stereoisomer of difethialone, said proportion being less than 50%—especially less than 25%, preferentially between 0% and 25%, in particular less than 10%—relative to the amount of said homo-stereoisomer of difethialone.

Advantageously and according to the invention, the difethialone is predominantly in the laevorotatory enantiomer form of said homo-stereoisomer of difethialone. The composition comprises the laevorotatory enantiomer of said homo-stereoisomer of difethialone in a proportion greater than each of the proportions of each of the other enantiomers of difethialone relative to the difethialone.

Advantageously, in a composition according to the invention:
the ratio of the amount of laevorotatory enantiomer of said homo-stereoisomer of difethialone to the sum of the amounts of each of the enantiomers of said homo-stereoisomer of difethialone and of said hetero-stereoisomer of difethialone is greater than 0.25 (greater than 25%);
the ratio of the concentration of laevorotatory enantiomer of said homo-stereoisomer of difethialone to the sum of the concentrations of each of the enantiomers of said homo-stereoisomer of difethialone and of said hetero-stereoisomer of difethialone is greater than 0.25 (greater than 25%); and
the proportion of laevorotatory enantiomer of said homo-stereoisomer of difethialone in the composition is greater than the proportion of each of the enantiomers of said homo-stereoisomer of difethialone and of said hetero-stereoisomer of difethialone. In a composition according to the invention, the proportion of laevorotatory enantiomer of said homo-stereoisomer of difethialone in the composition is more than 25% relative to the difethialone.

Advantageously and according to the invention, the composition comprises an amount of the laevorotatory enantiomer of said homo-stereoisomer of difethialone such that the ratio of this amount to the amount of difethialone is greater than 25%, especially greater than 50%, in particular greater than 70%, more particularly greater than 80%, preferably greater than 90%, particularly preferentially greater than 95%, more preferentially greater than 98%, even more preferentially greater than 99% or about 100%. A composition according to the invention thus comprises difethialone predominantly in the laevorotatory enantiomer form of said homo-stereoisomer of difethialone.

Advantageously, the composition comprises an amount of the laevorotatory enantiomer of said homo-stereoisomer of difethialone such that the ratio of this amount to the amount of difethialone is greater than 70%, preferably between 80% and 100%, more preferentially between 90% and 100%, relative to the amount of difethialone. Advantageously, the composition comprises an amount of the laevorotatory enantiomer of said homo-stereoisomer of difethialone such that the ratio of this amount to the amount of difethialone is between 95% and 99%. Advantageously, the composition comprises an amount of the laevorotatory enantiomer of said homo-stereoisomer of difethialone such that the ratio of this amount to the amount of difethialone is between 96% and 100%. Advantageously, the composition comprises an amount of the laevorotatory enantiomer of said homo-stereoisomer of difethialone such that the ratio of this amount to the amount of difethialone is substantially about 100%.

Advantageously and according to the invention, the composition comprises an amount of the laevorotatory enantiomer of said homo-stereoisomer of difethialone such that the ratio of this amount to the amount of difethialone is greater than 95%.

A composition according to the invention may be substantially free of dextrorotatory enantiomer of said homo-stereoisomer of difethialone, i.e. the dextrorotatory enantiomer of said homo-stereoisomer of difethialone may be present in the composition, but only in trace amount. It may also be substantially free of said hetero-stereoisomer of difethialone, i.e. said hetero-stereoisomer of difethialone may be present in the composition, but only in trace amount.

Advantageously and according to the invention, the composition is in liquid form and comprises a liquid solvent for difethialone. It may be a solution of difethialone in a solvent for difethialone, with the exclusion of a racemic mixture of said laevorotatory and dextrorotatory enantiomers of said homo-stereoisomer of difethialone. It may also be a solution comprising difethialone in a solvent for difethialone and in which said homo-stereoisomer of difethialone is predominantly in laevorotatory enantiomer form. It may also be a solution comprising difethialone in a solvent for difethialone and in which the difethialone is predominantly in the laevorotatory enantiomer form of said homo-stereoisomer of difethialone. It may also be a suspension or an emulsion of difethialone in a liquid medium.

Advantageously and according to the invention, the composition is in solid form. It may also be a solid comprising difethialone, with the exclusion of a racemic mixture of the dextrorotatory and laevorotatory enantiomers of said homo-stereoisomer of difethialone. It may also be a solid comprising difethialone and in which said homo-stereoisomer of difethialone is predominantly in laevorotatory enantiomer form. It may also be a solid comprising difethialone and in which the difethialone is predominantly in the laevorotatory enantiomer form of said homo-stereoisomer of difethialone.

The invention thus also relates to a composition comprising difethialone, the difethialone of the composition being optically active. However, it is not excluded for the difethialone of the composition according to the invention to be optically inactive.

The invention also relates to the use of a composition according to the invention for the preparation of a rodenticidal bait for target rodent pests.

The invention also relates to a rodenticidal bait comprising a composition according to the invention, and at least one excipient that is edible for target rodent pests.

A rodenticidal bait according to the invention comprises:
at least one excipient that is edible for target rodent pests,
the laevorotatory enantiomer of the configurational stereoisomer of difethialone, named homo-stereoisomer, of formula 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said homo-stereoisomer have the same absolute configuration, with the exclusion of a racemic mixture of laevorotatory and dextrorotatory enantiomers of said homo-stereoisomer of difethialone. In a bait according to the invention, the laevorotatory enantiomer of said homo-stereoisomer of difethialone and the dextrorotatory enantiomer of said homo-stereoisomer of difethialone are in different amounts.

Advantageously, a rodenticidal bait according to the invention comprises an excipient that is edible for target rodent pests and said homo-stereoisomer of difethialone predominantly in laevorotatory enantiomer form.

The inventors who succeeded in separating the laevorotatory enantiomer and the dextrorotatory enantiomer of said homo-stereoisomer of difethialone and the enantiomers of said hetero-stereoisomer of difethialone and in obtaining the laevorotatory enantiomer of said homo-stereoisomer of difethialone in isolated form discovered that said homo-stereoisomer of difethialone is in fact the configurational stereoisomer of difethialone that has the lower hepatic persistence in target rodent pests. They also observed that the laevorotatory enantiomer of said homo-stereoisomer of difethialone is the enantiomer—among the two enantiomers (laevorotatory and dextrorotatory) of said homo-stereoisomer of difethialone—that is the more persistent in the liver of target rodent pests. However, they also discovered that this laevorotatory enantiomer of said homo-stereoisomer of difethialone has higher persistence in the liver of target rodent pests than that of said homo-stereoisomer of difethialone.

The laevorotatory enantiomer of said homo-stereoisomer of difethialone in fact makes it possible to efficiently control target rodent pests and in particular with reduced doses of difethialone. The laevorotatory enantiomer of said homo-stereoisomer of difethialone constitutes an alternative of choice for producing a rodenticidal bait which has acceptable rodenticidal efficacy—especially at low dose—and acceptable ecotoxicity. It also constitutes an alternative for producing rodenticidal baits for the purpose of controlling target rodent pests that are liable to be resistant to known rodenticidal baits.

Advantageously and according to the invention, the rodenticidal bait comprises a mass amount of difethialone such that the ratio (mass proportion) of this mass amount of difethialone to the mass amount of rodenticidal bait is less than 200 ppm, i.e. less than 200 mg of difethialone per kilogram of rodenticidal bait. Advantageously, the mass proportion of difethialone in the rodenticidal bait is between 1 ppm and 100 ppm (1 mg to 100 mg of difethialone per kilogram of rodenticidal bait), especially between 5 ppm and 100 ppm (5 mg to 100 mg of difethialone per kilogram of rodenticidal bait), preferably between 5 ppm and 50 ppm (5 mg to 50 mg of difethialone per kilogram of rodenticidal bait), more preferentially between 10 ppm and 50 ppm (10 mg to 50 mg of difethialone per kilogram of rodenticidal bait), even more preferentially between 15 ppm and 50 ppm (15 mg to 50 mg of difethialone per kilogram of rodenticidal bait).

Advantageously and according to the invention, the excipient that is edible for target rodent pests is chosen to allow consumption of the bait by target rodent pests. Advantageously and according to the invention, each edible excipient is non-lethal to target rodent pests. The edible excipient is not in itself rodenticidal.

Advantageously and according to the invention, the edible excipient comprises at least one food chosen from the group formed from cereal seeds—especially hulled cereal seeds—cereal seed meals, cereal seed flours, cereal seed flakes, cereal bran and non-cereal seeds, for example alfalfa seeds, especially in hulled form, in the form of meal, in the form of flour, or in the form of flakes or bran. The edible excipient may comprise any support that can be consumed by target rodent pests.

Advantageously, the edible excipient comprises at least one food chosen from the group formed from foods of plant origin and foods of animal origin. Advantageously, the edible excipient comprises at least one food chosen to stimulate the appetite of the target rodent pests. In particular, this food is chosen from the group formed from seeds of one or more cereals, hulled seeds of one or more cereals, meals of seeds of one or more cereals, flakes of seeds of one or more cereals, bran of one or more cereals and flour of seeds of one or more cereals. By way of example, the cereals are chosen from the group formed from oat, wheat, barley, corn, soybean and rice.

Advantageously, the food is chosen from the group formed from sweetened foods. For example, they may be foods comprising at least one sugar chosen from the group formed from sucrose, lactose, fructose and glucose. It may be a sugar syrup—for example a sugar syrup obtained by hydrolysis of starch—or a sugar syrup obtained by hydrolysis of sucrose (invert sugar syrup), or a beet sugar syrup, or a maple syrup or a sugarcane syrup, or a syrup obtained from a plant of the Stevia genus.

Advantageously, the food is chosen from the group formed from coconut albumen (copra) flakes and flour. Advantageously, the food is chosen from the group formed from walnuts, hazelnuts and almonds—in grated and/or powder form.

Advantageously, the food is chosen from the group formed from plant fats, plant oils (for example rapeseed oil, soybean fat, sunflower oil, cocoa butter, groundnut oil, groundnut butter, corn oil, palm oil), animal fats and animal oils (butter, lard, fish oil).

Advantageously, the food is chosen from the group formed from proteins of plant origin and proteins of animal origin. By way of example, examples that may be mentioned include powdered milk—especially powdered skimmed milk—eggs—especially powdered eggs—protein hydrolysates of animal origin and protein hydrolysates of plant origin.

Advantageously and according to the invention, the rodenticidal bait is chosen from the group formed from solid baits comprising difethialone and a solid edible excipient. Advantageously, the rodenticidal bait is a solid in divided form, for example in the form of balls or granules. Advantageously, the rodenticidal bait may be a solid in block or paste form that may be consumed by the target rodent pests or a solid material that may be nibbled by the target rodent pests. Advantageously, the solid rodenticidal bait according to the invention may be in the form of a rigid block, a semi-rigid block, a foam, a powder or a gel.

Advantageously, the rodenticidal bait which is in the form of a powder, in the form of a foam or in the form of a gel is suitable for soiling the fur of the target rodent pest(s) and for being ingested by said pest(s) during their grooming.

It may be a solid rodenticidal bait comprising difethialone, with the exclusion of a racemic mixture of the dextrorotatory and laevorotatory enantiomers of said homo-stereoisomer of difethialone. It may also be a solid rodenticidal bait comprising difethialone and in which said homo-stereoisomer of difethialone is predominantly in laevorotatory enantiomer form. It may also be a solid rodenticidal bait comprising difethialone in which the difethialone is predominantly in the laevorotatory enantiomer form of said homo-stereoisomer of difethialone.

Advantageously and according to the invention, the rodenticidal bait is chosen from the group formed from liquid baits comprising difethialone and a liquid edible excipient. The rodenticidal bait is then a drink for target rodent pests.

Advantageously and according to the invention, the rodenticidal bait is chosen from the group formed from liquid baits comprising difethialone and a liquid edible excipient. The rodenticidal bait is then a drink for target rodent pests. It may be a solution of difethialone in a solvent for difethialone, with the exclusion of a racemic mixture of dextrorotatory and laevorotatory enantiomers of said homo-stereoisomer of difethialone. It may also be a solution of difethialone in a solvent for difethialone and in which said homo-stereoisomer of difethialone is predominantly in laevorotatory enantiomer form. It may also be a solution of difethialone in a solvent for difethialone and in which the difethialone is predominantly in the laevorotatory enantiomer form of said homo-stereoisomer of difethialone.

The invention thus also relates to a rodenticidal bait in which the difethialone is optically active. However, it is not excluded for the difethialone of the rodenticidal bait according to the invention to be optically inactive.

Advantageously, the rodenticidal bait comprises at least one dye. Such a dye makes it possible in particular to give said rodenticidal bait a colour that is readily detectable and identifiable by a person handling the rodenticidal bait.

Advantageously, the rodenticidal bait comprises at least one preserving agent capable of ensuring its conservation during its storage. Advantageously, the rodenticidal bait comprises at least one bittering compound such as denatonium benzoate, also known as Bitrex®, which is intended to reduce the risks of accidental consumption by non-target organisms.

Advantageously, in one particular variant, the composition and the rodenticidal bait according to the invention exclusively comprise difethialone as rodenticidal substance. In particular, the composition and the rodenticidal bait according to the invention are free of any other anticoagulant substance for rodenticidal use. However, in this variant according to the invention, the composition and the rodenticidal bait may comprise any pest-control substance other than a rodenticide, such as an insecticidal and/or acaricidal substance.

Advantageously, in another particular variant, the composition and the rodenticidal bait according to the invention comprise difethialone with the exclusion of a racemic mixture of laevorotatory and dextrorotatory enantiomers of said homo-stereoisomer and at least one other substance different from difethialone as rodenticidal substance. This other rodenticidal substance different from difethialone may be another anticoagulant substance—especially of the anti-vitamin K type or not—or another non-anticoagulant rodenticidal substance.

The invention also relates to a process for controlling target rodent pests, in which there is spread an amount of rodenticidal bait comprising:
  at least one excipient that is edible for target rodent pests; and
  the laevorotatory enantiomer of the configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration;
  with the exclusion of a racemic mixture of the laevorotatory and dextrorotatory enantiomers of said homo-stereoisomer of difethialone.

The invention also relates to a process for controlling target rodent pests, in which there is spread an amount of rodenticidal bait according to the invention, said amount of bait being sufficient to be rodenticidal.

An amount of rodenticidal bait comprising said homo-stereoisomer of difethialone predominantly in laevorotatory enantiomer form, which has acceptable rodenticidal efficacy even at a low dose of difethialone, is thus spread. The process according to the invention thus makes it possible to limit the secondary poisoning of non-rodent mammals and birds that are liable to feed on poisoned rodents which are dead or alive but comprising a reduced amount—and especially a non-lethal amount—of difethialone. The process according to the invention also makes it possible to limit such secondary poisoning of non-rodent mammals and birds that are liable to preferentially consume the viscera—in particular the liver—of said dead or live poisoned rodents.

Advantageously, in a process according to the invention, said homo-stereoisomer of difethialone is predominantly in laevorotatory enantiomer form. Advantageously, the difethialone is predominantly in the laevorotatory enantiomer form of said homo-stereoisomer of difethialone.

Advantageously and as a variant according to the invention, the following are chosen in combination:
the edible excipient;
a proportion of laevorotatory enantiomer of said homo-stereoisomer of difethialone relative to said homo-stereoisomer of difethialone;
a proportion of laevorotatory enantiomer of said homo-stereoisomer of difethialone relative to the difethialone;
a mass proportion of difethialone relative to the rodenticidal bait; and
an amount of spread bait;
so that target rodent pests consume an amount of difethialone that is sufficient to be lethal to said target rodent pests which consume said bait in the course of a single period of 24 consecutive hours.

A rodenticidal bait according to this variant of the invention is a bait that is mortal in a single intake, or a "one-shot" bait. Advantageously and according to this variant of the invention, the mass proportion of difethialone in the bait is between 5 ppm and 200 ppm, especially between 5 ppm and 100 ppm, preferably between 5 ppm and 50 ppm, more preferentially between 15 ppm and 50 ppm.

Advantageously and in another variant according to the invention, the following are chosen in combination:
the edible excipient;
a proportion of laevorotatory enantiomer of said homo-stereoisomer of difethialone relative to said homo-stereoisomer of difethialone;
a proportion of laevorotatory enantiomer of said homo-stereoisomer of difethialone relative to the difethialone;
a mass proportion of difethialone relative to the rodenticidal bait; and
an amount of spread bait;
so that target rodent pests consume an amount of difethialone:
which is non-lethal to target rodent pests, i.e. which is generally non-lethal to target rodent pests, which consume said bait over a period of 24 consecutive hours; and
which is sufficient to be lethal to target rodent pests which consume said bait over several 24-hour periods, said periods being consecutive.

This other variant of the invention is thus directed towards a process for controlling target rodent pests, in which there is spread an amount of rodenticidal bait that is lethal for target rodent pests which durably consume this rodenticidal bait and non-lethal for non-target rodents or animals which accidentally consume this rodenticidal bait. This is then referred to as a "multi-dose" or "multi feeding" control process. In such a process according to the invention, the consumption of rodenticidal bait by a target rodent pest over a period of 24 hours is insufficient to result in the death of said rodent, whereas repeated consumption of rodenticidal bait over at least two consecutive days can result in the death of the target rodent pest. In addition, the accidental consumption of rodenticidal bait by a non-target animal or a human over a period of 24 hours is usually insufficient to lead to the death of said animal or of a human.

The invention is thus directed towards a process for controlling target rodent pests, in which target rodent pests are provided with an amount of rodenticidal bait that is liable to be ingested by the target rodent pests, said amount of rodenticidal bait being sufficient to kill target rodent pests which consume said rodenticidal bait over several days.

Advantageously, the amount of rodenticidal bait spread, the mass proportion of difethialone relative to the rodenticidal bait and the proportion of laevorotatory enantiomer of said homo-stereoisomer of difethialone relative to the difethialone are adapted so that the consumption of the rodenticidal bait is lethal to target rodent pests which daily consume bait over at least two 24-hour periods, especially from 3 to 7 periods.

Advantageously, in this other variant of the invention, an amount of rodenticidal bait is spread so that target rodent pests consume an amount of difethialone that is sufficient to be lethal to said target rodent pests which consume said bait over several 24-hour periods, said periods being consecutive.

Advantageously, in this other variant of a process according to the invention, the amount of laevorotatory enantiomer of said homo-stereoisomer of difethialone is such that since the ratio of this amount to the amount of difethialone is greater than 95%, especially about 100%, the mass proportion of difethialone relative to the rodenticidal bait is between 5 ppm and 50 ppm, especially between 10 ppm and 15 ppm.

In a process according to the invention, target rodent pests are provided with an amount of rodenticidal bait that is sufficient to satisfy their daily appetite, said rodenticidal bait comprising a major proportion of laevorotatory enantiomer of said homo-stereoisomer of difethialone.

In a process according to the invention, the amount of rodenticidal bait spread, the proportion of the laevorotatory enantiomer of said homo-stereoisomer of difethialone relative to the difethialone and the mass proportion of difethialone relative to the rodenticidal bait are adapted so as to allow consumption of rodenticidal bait for several days by target rodent pests, while at the same time limiting:
the risks of primary intoxication of non-target mammals and birds which are liable to consume such a rodenticidal bait only occasionally and accidentally;
the risks of secondary intoxication, for example of predators of target rodents, which are liable to consume target rodents—dead or live—that have ingested an amount of said bait.

Advantageously and according to the invention, the amount of bait spread, the ratio of the mass of difethialone to the mass of the rodenticidal bait, the ratio of the amount of the laevorotatory enantiomer of said homo-stereoisomer of difethialone to the amount of said homo-stereoisomer of difethialone and the ratio of the amount of the laevorotatory enantiomer of said homo-stereoisomer of difethialone to the amount of difethialone are adapted to minimize the (total) amount of difethialone in the liver of the target rodent pests.

The invention also relates to a chromatographic process for obtaining a laevorotatory enantiomer of a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said homo-stereoisomer have the same absolute configuration, in which process:

a high-pressure liquid chromatography column of dimensions 150×2 mm, and comprising a chiral stationary phase constituted of cellulose tris(4-methylbenzoate) particles, said particles having a mean size of 3 μm and having a mean pore size of 1000 Å, is chosen;

a mixture formed from acetonitrile (A) and water comprising 0.1% by volume of formic acid (B), with an A/B volume ratio of 80/20 and with a flow rate of the liquid mobile phase in the chromatography column of 0.25 mL/minute, is chosen as liquid mobile phase;

separation of the configurational stereoisomers of difethialone is performed at room temperature, during which:

a liquid composition comprising said laevorotatory enantiomer of said homo-stereoisomer of difethialone is introduced into the top of the chromatography column; and then the liquid composition is entrained with the mobile phase in the chromatography column under conditions suitable for separating the configurational stereoisomers of difethialone; and a fraction of the mobile phase comprising said laevorotatory enantiomer of said homo-stereoisomer of difethialone is collected with a retention time $t_1$ having a value such that $t_1 < t_2 < t_3 < t_4$; $t_2$, $t_3$ and $t_4$ representing the retention times of each of the configurational stereoisomers of difethialone different from the laevorotatory enantiomer of said homo-stereoisomer of difethialone, separately from a dextrorotatory enantiomer of said homo-stereoisomer of difethialone with a retention time $t_4$ and separately from the laevorotatory and dextrorotatory enantiomers of a configurational stereoisomer of difethialone, named hetero-stereoisomer, in which carbons 1 and 3 of the 1,2,3,4-tetrahydronaphthalene group of said hetero-stereoisomer have different absolute configurations, and of retention times $t_2$ and $t_3$; and then the liquid mobile phase of said fraction is removed so as to obtain said laevorotatory enantiomer of said homo-stereoisomer of difethialone.

The invention also relates to a configurational stereoisomer of difethialone, to a process for obtaining such a configurational stereoisomer, to a composition comprising such a configurational stereoisomer, to a rodenticidal bait and to a process for controlling target rodent pests, which are characterized in combination by all or some of the characteristics mentioned hereinabove or hereinbelow.

Other aims, characteristics and advantages of the invention will emerge on reading the following description and the examples, which are given for purely non-limiting purposes and which refer to the attached figures, in which.

Figure 8:
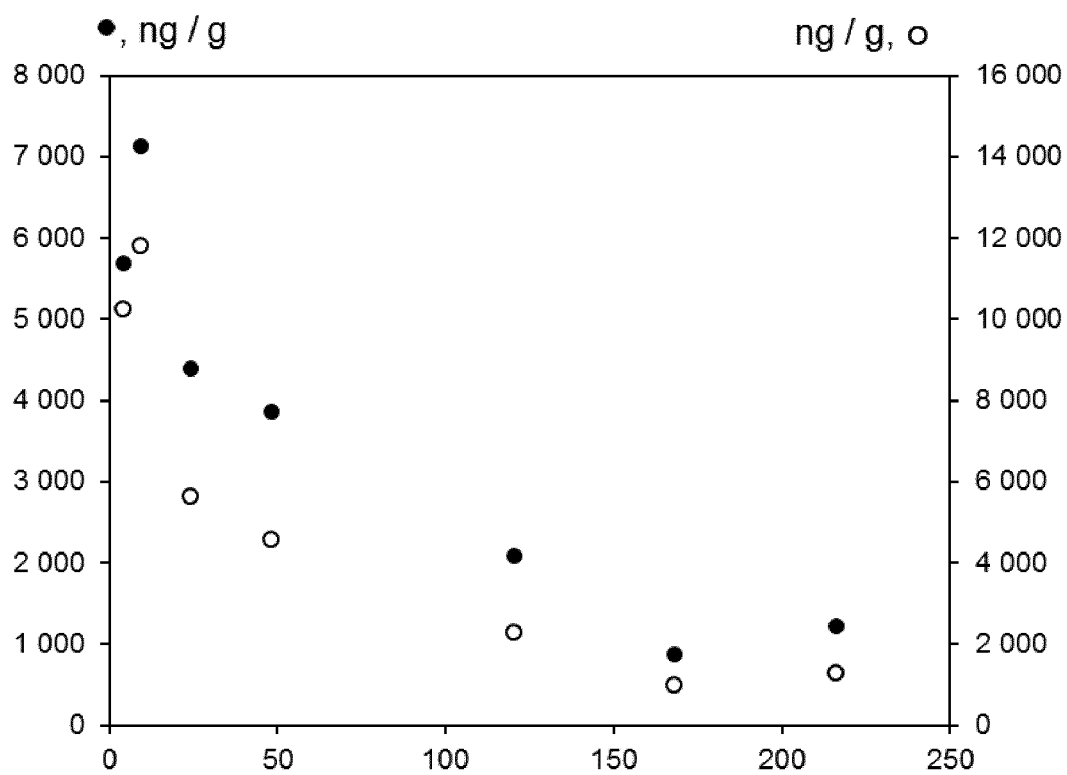
Figure 9:
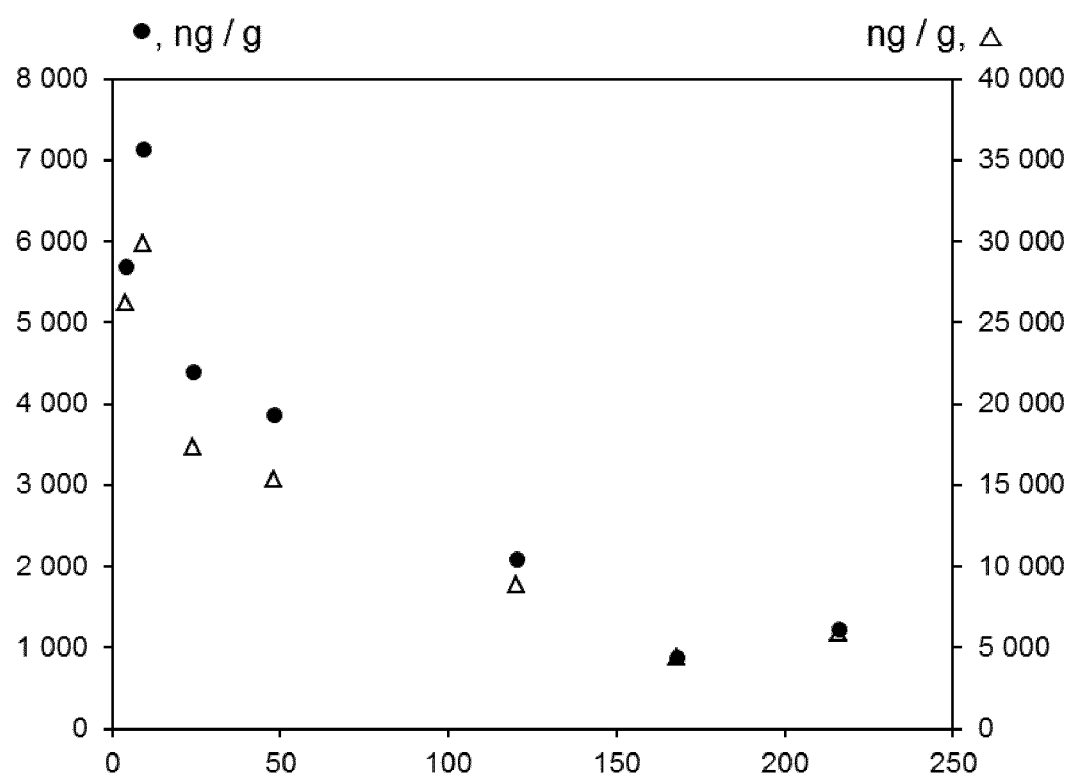

FIG. 8 is a representation in graph form of the change over time of the hepatic concentration in rats (male and female) of the laevorotatory enantiomer of said homo-stereoisomer of difethialone (●) and of said homo-stereoisomer of difethialone (○); and FIG. 9 is a representation in graph form of the change over time of the hepatic concentration in rats (male and female) of the laevorotatory enantiomer of said homo-stereoisomer of difethialone (●) and of the total difethialone (Δ).

Figure 2:
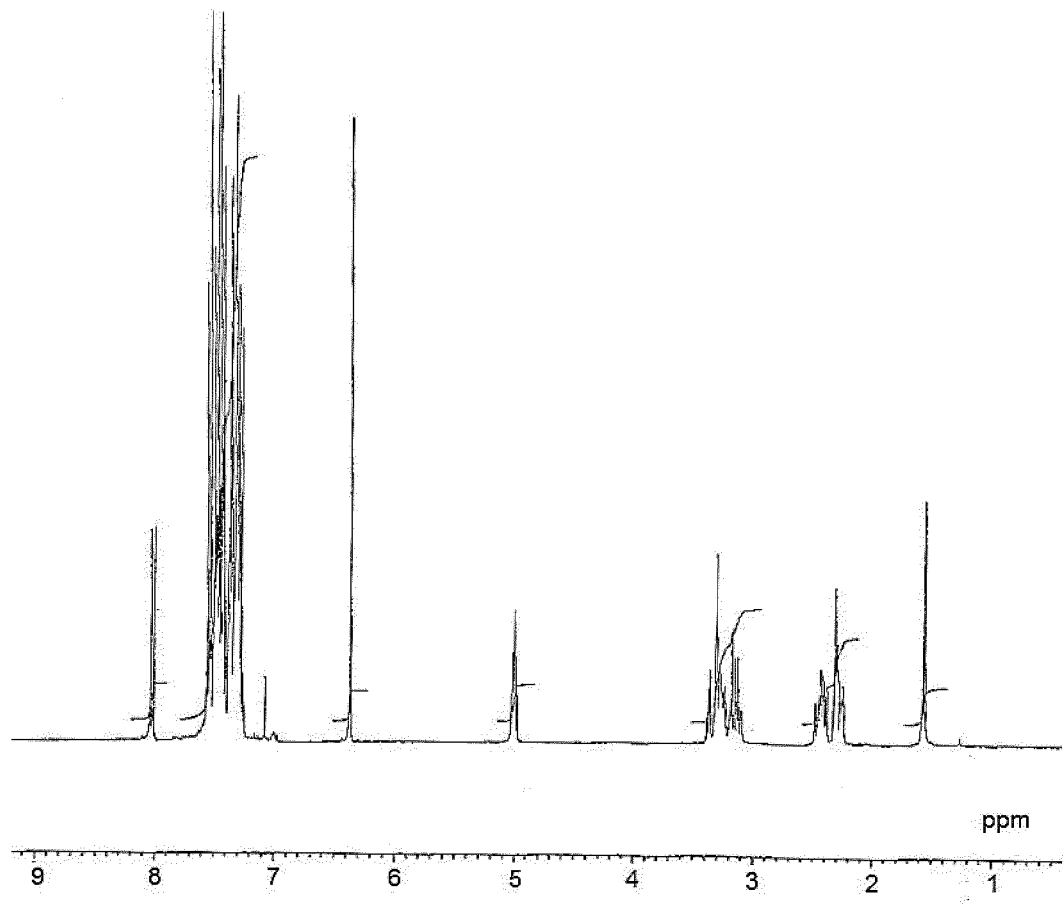
FIG. 2 is a proton NMR spectrum at 300 MHz of said homo-stereoisomer of difethialone.

A. Purification of the Laevorotatory Enantiomer of said Isolated Homo-Stereoisomer of Difethialone A.1. Identification of said Homo-Stereoisomer of Difethialone The homo-stereoisomer of difethialone is identified by proton magnetic resonance ($^1H$-NMR) spectroscopy. The homo-stereoisomer of difethialone dissolved in $CDCl_3$ has a multiplet at a chemical shift (δ) of between 4.9 ppm and 5.1 ppm and corresponding to the proton borne by carbon 1 of the 1,2,3,4-tetrahydronaphthalene group of difethialone as illustrated in FIG. 2.

The hetero-stereoisomer of difethialone and the homo-stereoisomer of difethialone are distinguished by their proton NMR spectra. In the proton NMR spectrum acquired in $CDCl_3$, the chemical shift of the proton borne by carbon 1 of the 1,2,3,4-tetrahydronaphthalene group of said hetero-stereoisomer of difethialone (FIG. 3) is between 5.2 ppm and 5.4 ppm.

A.2. Separation of the Laevorotatory and Dextrorotatory Enantiomers of said Homo-Stereoisomer of Difethialone by High-Pressure Liquid Chromatography The inventors solved the complex problem, which was not solved to date, of the separation of the laevorotatory and dextrorotatory enantiomers of said homo-stereoisomer of difethialone from a commercial preparation of difethialone. They succeeded in performing an analytical separation of the enantiomers of said homo-stereoisomer of difethialone by high-pressure (high-performance) liquid chromatography on a LUX® Cellulose-3 chiral column (Phenomenex, Le Pecq, France) of dimensions 150×2 mm and comprising a chiral stationary phase constituted of porous particles of cellulose tris(4-methylbenzoate), with a particle size of 3 μm and a porosity of 1000 Å and using, as mobile phase, an eluent formed from a mixture of acetonitrile (A) and water comprising formic acid in a volume proportion of 0.1% in water (B), with an A/B volume proportion of 80/20. The flow rate of the mobile phase in the column is 0.25 mL/minute and the separation is performed at a temperature of 23.2° C. The solution containing the sample to be analysed is at a concentration of 1 μg of difethialone per millilitre in acetonitrile and is filtered through a regenerated cellulose membrane with a cut-off threshold of 0.2 μm. The volume of solution containing the sample to be analysed injected onto the column is 1 μL.

Figure 1:
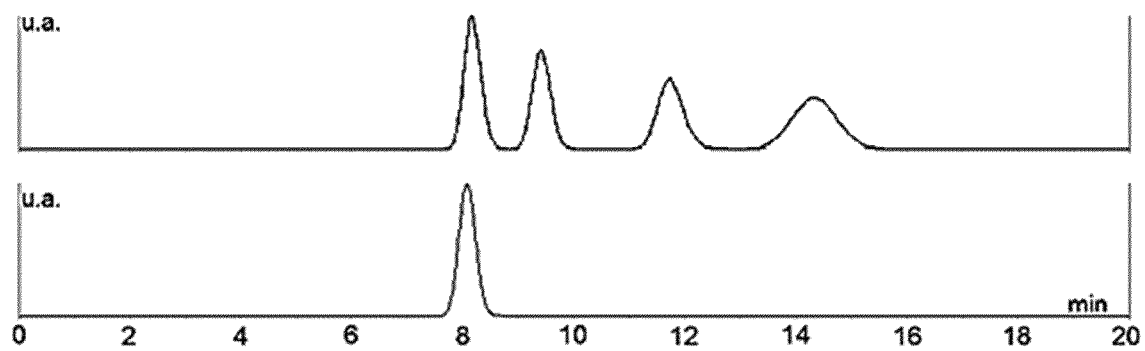
FIG. 1 is a chromatogram of an analysis by high-pressure liquid chromatography on a chiral column of difethialone (top) and of the laevorotatory enantiomer of said purified homo-stereoisomer of difethialone (bottom)

In a process for separating the enantiomers of said homo-stereoisomer of difethialone, it is possible to detect said enantiomers leaving the column by tandem mass spectrometry (MS/MS) in negative electrospray ionization mode (ESI: ElectroSpray Ionization). The temperature of the carrier gas is 350° C. and its flow rate is 8 L/minute. The pressure of the nebulizer is brought to 2700 hPa. In particular, the MRM ("Multiple Reaction Monitoring") transitions m/z 537.1→151.0 and m/z 537.1→78.9, corresponding to the difethialone signals, are analysed. FIG. 1 represents the chromatograms of difethialone (top) and of the laevorotatory enantiomer of the isolated homo-stereoisomer of difethialone (bottom).

Under these experimental conditions, the value of the retention time ($t_1$) for the laevorotatory enantiomer of said homo-stereoisomer according to the invention is about 8.1 minutes as described in FIG. 1. By way of comparison, the value of the retention time ($t_4$) for said dextrorotatory enantiomer of said homo-stereoisomer according to the invention is about 14.4 minutes, such that the dextrorotatory and laevorotatory enantiomers of said homo-stereoisomer may be efficiently separated by high-pressure liquid chromatography on a chiral column.

The value of the retention time ($t_3$) for the dextrorotatory enantiomer of said hetero-stereoisomer of difethialone is about 11.7 minutes and the value of the retention time ($t_2$) for the laevorotatory enantiomer of said hetero-stereoisomer of difethialone is about 9.4 minutes. Thus, under these experimental conditions, the order of elution of the difethialone enantiomers is such that $t_1<t_2<t_3<t_4$.

It is possible under these experimental conditions (stationary phase, mobile phase, temperature) to perform a preparative separation of the laevorotatory and dextrorotatory enantiomers of said homo-stereoisomer of difethialone by using a similar stationary phase with a particle size of greater than 3 μm, and a chromatography column of larger dimensions, especially a diameter of 20 mm.

B. Structural Characterization

B.1. UV Spectroscopy

The UV spectrum of the laevorotatory enantiomer of said homo-stereoisomer of difethialone dissolved in chloroform ($CHCl_3$) shows absorbance peaks at 238.2 nm and 259.5 nm.

B.2. Optical Rotation

The inventors characterized the laevorotatory enantiomer of said homo-stereoisomer of difethialone in isolated form by means of its optical rotation (also known as the optical activity or circular birefringence), i.e. its ability to deviate the polarization plane of polarized light. Deviation of the polarization plane of polarized light clockwise facing the polarized light beam characterizes an optically active and dextrorotatory solution and compound, and deviation of the polarization plane of polarized light anticlockwise facing the polarized light beam characterizes an optically active and laevorotatory solution and compound.

The optical rotation of a solution of laevorotatory enantiomer of said homo-stereoisomer of difethialone in chloroform ($CHCl_3$) is measured at a concentration of 11.05 g/L. The optical rotation of this solution is measured by means of a P 2000 digital polarimeter (JASCO, Bouguenais, France) operating with excitatory light with a wavelength of 589 nm. The mean optical rotation α obtained on two series of 10 measurements is −1.635°. The specific optical rotation at 25° C. $[\alpha]^{25°C}_{589\,nm}$ for the laevorotatory enantiomer of said homo-stereoisomer of difethialone dissolved in chloroform, measured on the sodium D line (589 nm), is −14.8°.

B.3. Circular Dichroism

Figure 7:
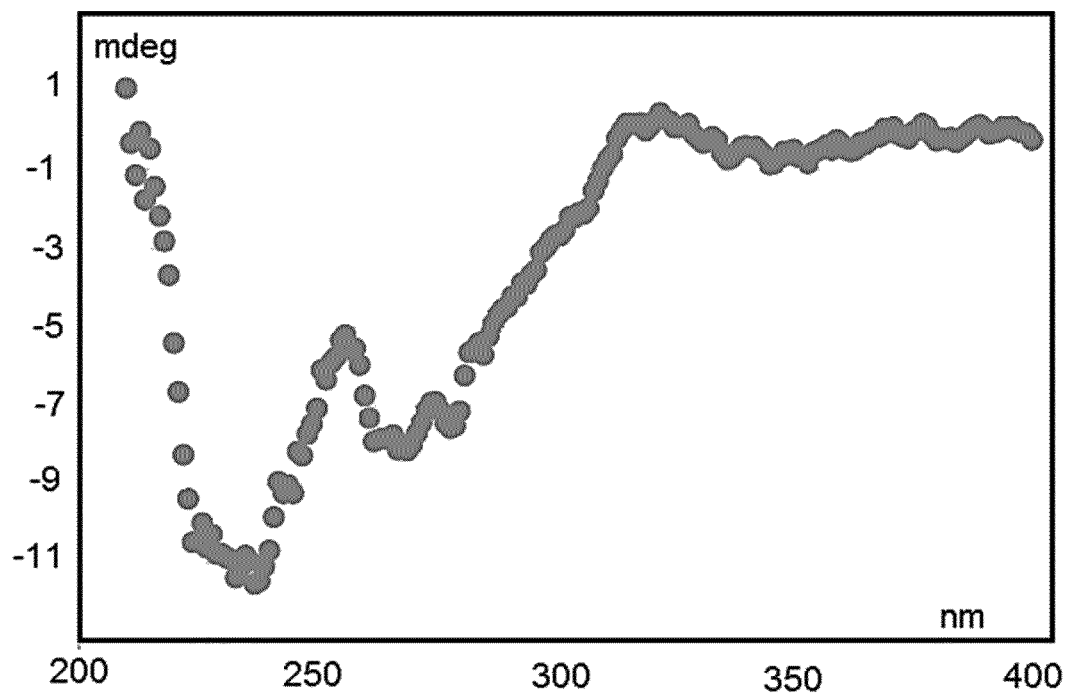
FIG. 7 is a circular dichroism spectrum of the laevorotatory enantiomer of said homo-stereoisomer of difethialone.

The circular dichroism spectrum of the laevorotatory enantiomer of said isolated homo-stereoisomer of difethialone reflects the difference in absorbance ($\Delta A=A_L-A_R$) of the two waves of left circular polarization (LCP) of intensity $A_L$ and of right circular polarization (RCP) of intensity $A_R$. This makes it possible to distinguish the dextrorotatory and laevorotatory enantiomers of said homo-stereoisomer of difethialone. This difference in absorbance of the two circularly polarized waves is measured in a J-815 circular dichroism spectrometer (JASCO, Bouguenais, France). 2 mL of a solution of laevorotatory enantiomer of said homo-stereoisomer of difethialone in methanol ($CH_3OH$) at a concentration of 0.81 mg/mL are prepared. The solution is transferred into a quartz spectrophotometer cuvette. The circular dichroism spectrum of the solution is measured at 25° C. between 200 nm and 400 nm. The circular dichroism spectrum of the laevorotatory enantiomer of said homo-stereoisomer of difethialone measured under these conditions is shown in FIG. 7. The circular dichroism value is negative between the wavelengths of 220 nm and 300 nm.

B.4. Nuclear Magnetic Resonance

Figure 3:
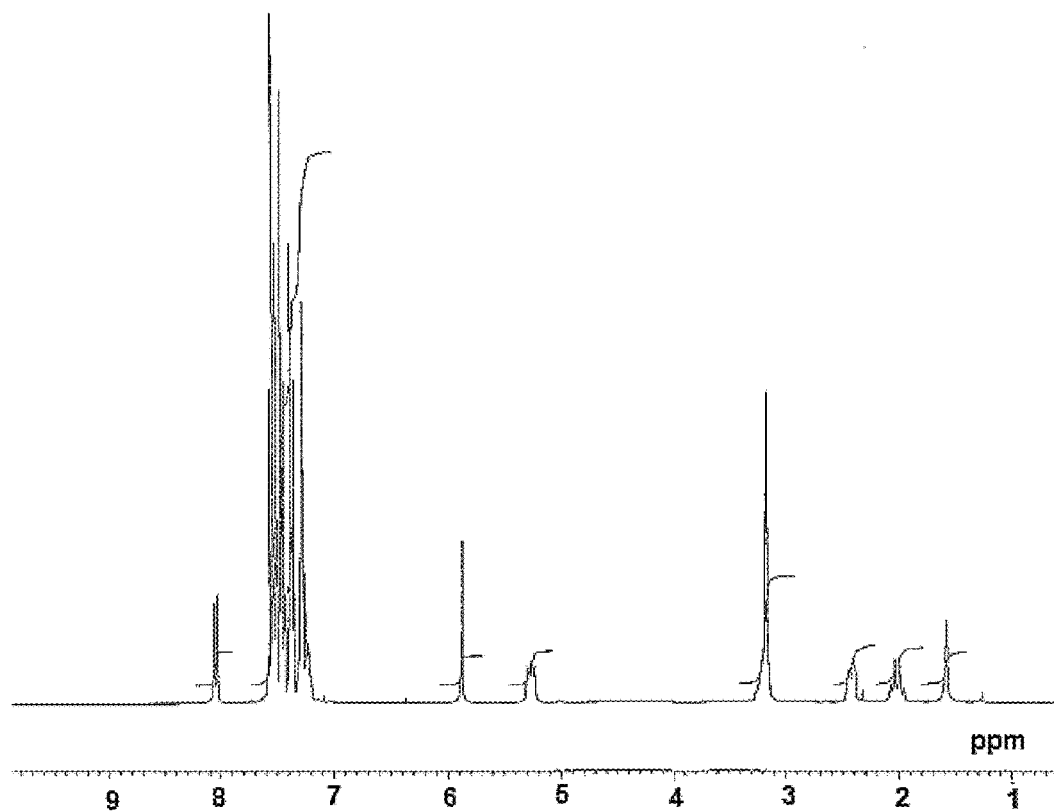
FIG. 3 is a proton NMR spectrum at 300 MHz of said hetero-stereoisomer of difethialone.

FIGS. 2 and 3 represent, respectively, a proton nuclear magnetic resonance spectrum ($^1$H-NMR) at 300 MHz of the homo-stereoisomer of difethialone in $CDCl_3$ (FIG. 2) and a proton nuclear magnetic resonance spectrum at 300 MHz in $CDCl_3$ of the hetero-stereoisomer of difethialone in $CDCl_3$ (FIG. 3). Said homo-stereoisomer of difethialone has (FIG. 2) a multiplet whose chemical shift (δ) is between 4.9 ppm and 5.1 ppm, corresponding to carbon 1 of the 1,2,3,4-tetrahydronaphthalene group of said homo-stereoisomer of difethialone. Said hetero-stereoisomer of difethialone has (FIG. 3) a multiplet whose chemical shift (δ) is between 5.2 ppm and 5.4 ppm.

Figure 4:
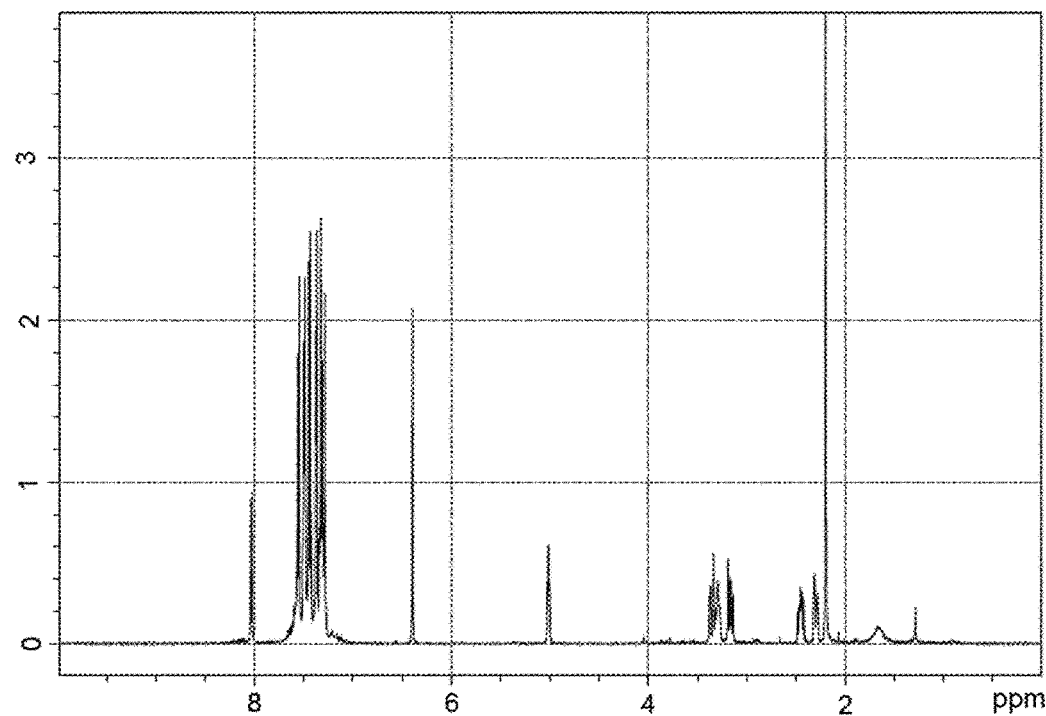
FIG. 4 is a proton NMR spectrum at 500 MHz of the laevorotatory enantiomer of said homo-stereoisomer of difethialone.

FIG. 4 is a proton NMR spectrum at 500 MHz of the laevorotatory enantiomer of said homo-stereoisomer of difethialone in $CDCl_3$. The proton NMR spectra of the dextrorotatory and laevorotatory enantiomers of said homo-stereoisomer of difethialone are indistinguishable from each other.

Figure 5:
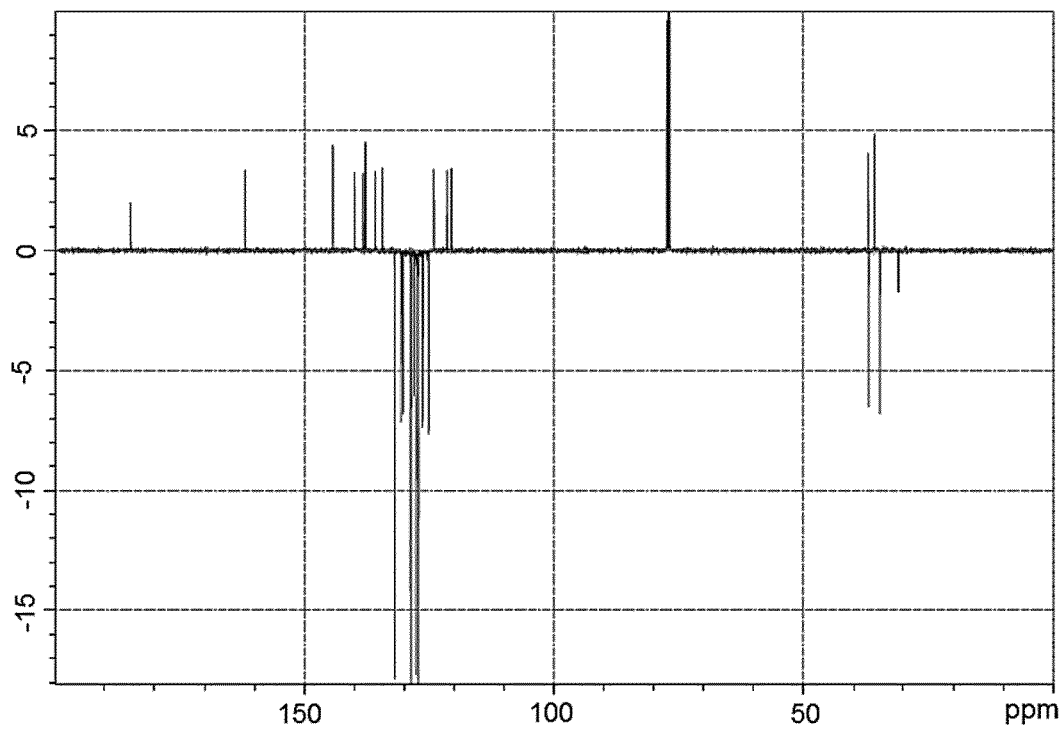
FIG. 5 is a $^{13}C$ carbon NMR spectrum at 500 MHz of the laevorotatory enantiomer of said homo-stereoisomer of difethialone.

FIG. 5 is a $^{13}$C NMR spectrum of the laevorotatory enantiomer of said homo-stereoisomer of difethialone dissolved in $CDCl_3$ at a concentration of 40 mg/mL, acquired on a Bruker Avance III HD spectrometer (500 MHz) equipped with a Prodigy motorized multi-core direct cryoprobe. It allows identification of the 31 carbon atoms of difethialone. The $^{13}$C-NMR spectrum of the laevorotatory enantiomer of said homo-stereoisomer of difethialone is not distinguished from the $^{13}$C-NMR spectrum of the dextrorotatory enantiomer of said homo-stereoisomer of difethialone. Said homo-stereoisomer of difethialone has a characteristic signal between 34 ppm and 38 ppm which is distinctive for said hetero-stereoisomer of difethialone.

Figure 6:
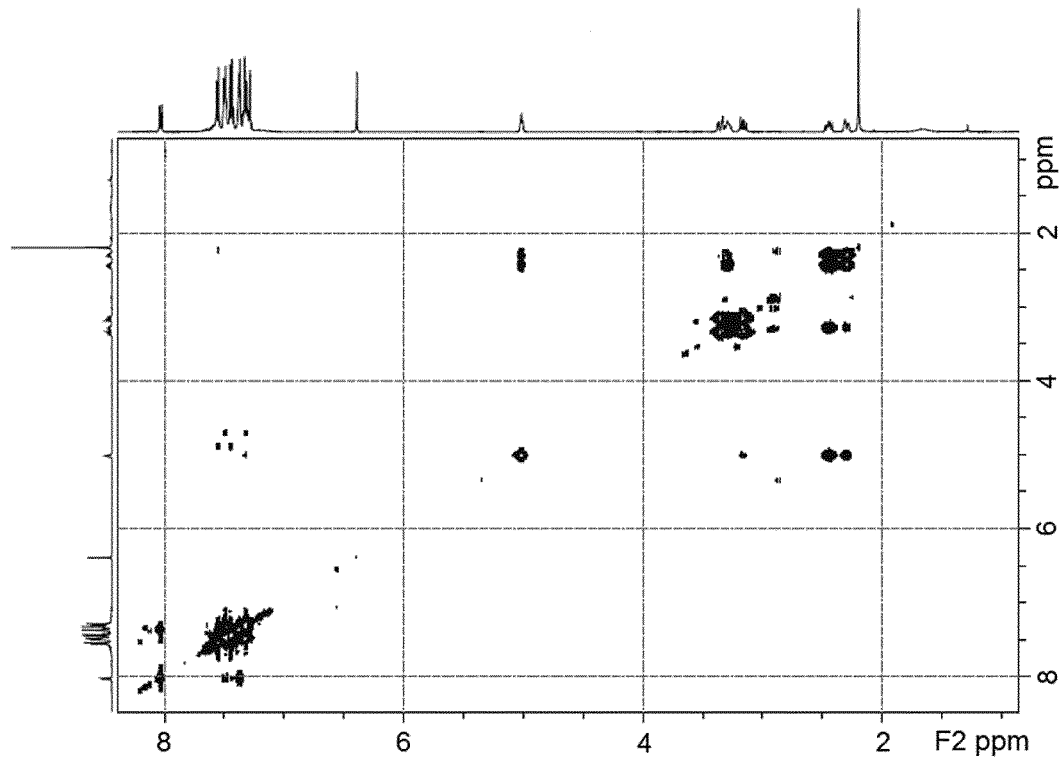
FIG. 6 is an analysis by proton NMR ($^1H$-NMR) correlation spectroscopy at 500 MHz of the laevorotatory enantiomer of said homo-stereoisomer of difethialone.

FIG. 6 is a two-dimensional proton NMR (2D $^1$H-NMR) spectrum obtained by correlation spectroscopy of the laevorotatory enantiomer of said homo-stereoisomer of difethialone dissolved in $CDCl_3$ at a concentration of 40 mg/mL acquired on a Bruker Avance III HD spectrometer (500 MHz) equipped with a Prodigy motorized multi-core direct cryoprobe. It allows identification of the coupling of the proton borne by carbon 1 of the 1,2,3,4-tetrahydronaphthalene group of said homo-stereoisomer of difethialone with the protons borne by carbon 2 of the 1,2,3,4-tetrahydronaphthalene group at 2.27 ppm.

C. Extraction of Difethialone from the Liver of Rats Treated with Difethialone for the Purpose of Analysis of the Various Enantiomers of Difethialone C.1. Homogenization of the Liver Sample About 0.525 g (±0.025 g) of rat liver is weighed out accurately and placed in a 50 mL polypropylene tube. 10 mL of acetone are added and the suspension is homogenized using an Ultra-Turrax® homogenizer/disperser for a time of about 30 seconds. The homogenizer/disperser shaft is rinsed with hot water and then twice with 20 mL of acetone in a polypropylene tube. The homogenate is centrifuged for 5 minutes at a centrifugation speed of 3000 rpm (revolutions per minute). The supernatant is collected and transferred into a test tube. The sample is subjected to evaporation under a stream of nitrogen ($N_2$) at a temperature of 40° C. so as to form a dry extract.

C.2. Lipid Removal 1 mL of acetonitrile is added to the tube containing the dry extract so as to dissolve it. The acetonitrile solution is washed twice successively with 1 mL of hexane. The lipid-free extract is dried under a stream of nitrogen ($N_2$) at a temperature of 40° C. and is then taken up in 0.5 mL of methanol and dissolved by vortex stirring. 0.5 mL of ultra-pure (Milli-Q) water is then added. The sample is vortex-homogenized.

C.3. Solid-Phase Extraction (SPE) of Difethialone 1 mL of dichloromethane ($CH_2Cl_2$), then 1 mL of methanol ($CH_3OH$), then 1 mL of ultra-pure (Milli-Q) water are passed through an Oasis HLB 1 cc cartridge (WAT094225, Waters). The lipid-free liver extract (1 mL MeOH/Milli-Q $H_2O$) containing difethialone is then loaded onto the top of the preconditioned cartridge. The liver extract penetrates through the cartridge by gravity on contact with the solid phase of the cartridge. 1 mL of washing solution formed from methanol ($CH_3OH$) and ultra-pure water ($H_2O$) in a 90/10 volume proportion is loaded onto the top of the cartridge. The cartridge is dried by suction under vacuum connected to the bottom of the cartridge. 1 mL of eluting solution formed from dichloromethane ($CH_2Cl_2$) and methanol ($CH_3OH$) in a 90/10 volume proportion is then loaded onto the top of the cartridge and an eluate comprising difethialone is collected at the bottom of the cartridge. The solvent of the eluate is evaporated off under a stream of nitrogen ($N_2$) at a temperature of 40° C. The sample is taken up in 0.5 mL of acetonitrile ($NC-CH_3$) and the acetonitrile solution containing difethialone is filtered through a 0.2 μm filter.

C.4. Analysis

The acetonitrile solution containing difethialone is analysed by high-pressure liquid chromatography on a LUX® Cellulose-3 chiral column (150×2 mm, particle size of 3 μm) (Phenomenex, Le Pecq, France) as described in point A2) above. The retention time value ($t_1$) of the laevorotatory enantiomer of said homo-stereoisomer of difethialone according to the invention is between 7.8 minutes and 8.4 minutes (the maximum value of the peak corresponding to the dextrorotatory enantiomer of said homo-stereoisomer being about 8.1 minutes, as described in FIG. 1), depending on the operating conditions, especially depending on the column temperature conditions. The retention time value ($t_4$) of the dextrorotatory enantiomer of said homo-stereoisomer is between 13.3 minutes and 15.1 minutes (the maximum value of the peak corresponding to the dextrorotatory enantiomer of said homo-stereoisomer being about 14.4 minutes), depending on the operating conditions, especially depending on the column temperature conditions. The retention time value ($t_3$) of the dextrorotatory enantiomer of said hetero-stereoisomer of difethialone is between 11.2 minutes and 12.3 minutes (the maximum value of the peak corresponding to the dextrorotatory enantiomer of said hetero-stereoisomer being about 11.7 minutes), depending on the operating conditions, especially depending on the column temperature conditions. The retention time value ($t_2$) of the laevorotatory enantiomer of said hetero-stereoisomer of difethialone is between 9.0 minutes and 9.8 minutes (the maximum value of the peak corresponding to the laevorotatory enantiomer of said hetero-stereoisomer being about 9.4 minutes), depending on the operating conditions, especially depending on the column temperature conditions. The composition of the sample is analysed by high-pressure liquid chromatography as described in point A2) above.

D. Study of the Hepatic Persistence of the Configurational Stereoisomers of Difethialone in Rats A solution of a mixture of said homo-stereoisomer and of said hetero-stereoisomer of difethialone in a mixture of vegetable oil and 5% DMSO is administered by tube-feeding ("per os") to male and female coumaphen-sensitive rats (*Rattus norvegicus*). The mole ratio of the amount of said homo-stereoisomer to the amount of said hetero-stereoisomer is 4/6. Each difethialone diastereoisomer is formed from a racemic mixture of the two enantiomers of the corresponding diastereoisomer.

The tube-feeding solution is administered (on D0) so that the amount of difethialone ingested by each rat is about 3.4 mg per kilogram of rat.

To avoid haemorrhage, the tube-fed rats are treated daily by subcutaneous administration of a dose of vitamin K1 (as haemorrhage antidote) at a rate of 0.1 U per 200 g of live rat weight.

At 4 hours (H+4), 9 hours (H+9), 24 hours (H+24), 120 hours (H+120), 168 hours (H+168) and 216 hours (H+216) after tube-feeding, three male rats and three female rats anaesthetized beforehand with isoflurane are euthanized, the liver of the euthanized rats is removed, the difethialone is then extracted from the liver and the amount of each of the configurational stereoisomers of difethialone is assayed via analysis by high-pressure liquid chromatography on a chiral column according to the process described above, the area under the peaks in the chromatogram obtained is measured and each enantiomer is quantified by comparison with a calibration curve. The following are assayed:

the dextrorotatory enantiomer of said homo-stereoisomer;
the laevorotatory enantiomer of said homo-stereoisomer according to the invention;
the dextrorotatory enantiomer of said hetero-stereoisomer;
the laevorotatory enantiomer of said hetero-stereoisomer; present in the liver of the tube-fed rats.

In FIGS. 8 and 9, the difethialone concentrations recorded (mean of the values measured on six rats and expressed in nanograms of enantiomer per gram of liver (ng/g) in the liver of the tube-fed rats) are given as a function of the time (in hours) after tube-feeding. In FIG. 8, the concentration of the laevorotatory enantiomer of said homo-stereoisomer according to the invention in the liver is represented by filled circles (●) on the left-hand scale and the concentration of said homo-stereoisomer of difethialone in the liver is represented by open circles (○) on the right-hand scale.

The laevorotatory enantiomer of said homo-stereoisomer according to the invention has inexplicably high hepatic persistence relative to the persistence of the homo-stereoisomer of difethialone.

In FIG. 9, the concentration of the laevorotatory enantiomer of said homo-stereoisomer according to the invention in the liver is represented by filled circles (●) on the left-hand scale and the total difethialone concentration in the liver is represented by open triangles (Δ) on the right-hand scale. The corresponding values are given in table 1 below.

TABLE 1

| Time after tube-feeding, hours | Hepatic content, ng/g Total difethialone | | | |
|---|---|---|---|---|
| | Homo-stereoisomer | | Hetero-stereoisomer | |
| | DFN-Homo-dextro | DFN-Homo-laevo | DFN-Hetero-dextro | DFN-Hetero-laevo |
| 4 | 4566 | 5692.5 | 10589.5 | 5380.5 |
| 9 | 4692.5 | 7141 | 12155.5 | 5869.5 |
| 24 | 1243.5 | 4403.5 | 8102 | 3613.5 |
| 48 | 720.5 | 3874 | 7974.5 | 2804 |
| 120 | 192.5 | 2087 | 5431.5 | 1211 |
| 168 | 129 | 878.5 | 3011 | 392.5 |
| 216 | 77.5 | 1224 | 4030.5 | 545 |

The laevorotatory enantiomer of said homo-stereoisomer according to the invention has high hepatic persistence relative to the persistence of difethialone.

Rodenticidal Bait Comprising a Proportion of 13.7 ppm of Difethialone

A pasty rodenticidal bait according to the invention is prepared by dispersing an amount of laevorotatory enantiomer of said homo-stereoisomer of difethialone in an edible excipient comprising vegetable fat and cereal flour. The measured proportion of difethialone relative to the bait is 13.7 ppm and the proportion of laevorotatory enantiomer of said homo-stereoisomer relative to the difethialone is 95.4% (13.1 mg of laevorotatory enantiomer of said homo-stereoisomer of difethialone per kilogram of bait). The bait also comprises a mass proportion of 3.3% of dextrorotatory enantiomer of said homo-stereoisomer of difethialone relative to the difethialone and a mass proportion of 1.4% of dextrorotatory enantiomer of said hetero-stereoisomer of difethialone relative to the difethialone.

On D0, ten coumaphen-sensitive Sprague-Dawley (SD) rats (five male rats and five female rats) are placed in individual cages with a rodenticide-free reference feed. On D3, each rat is weighed, and 50 g of rodenticidal bait as described above are then provided to each rat. This provision of 50 g of rodenticidal bait is renewed daily. The bait consumed by the rats is made up to 50 g of bait on D4, D5 and D6. The weight gain of each of the rats is also measured daily. Starting from D7, the residual rodenticidal baits are removed and rodenticide-free feed is provided to all the rats. The rats are monitored for 3 weeks.

The mean amounts of bait consumed daily by a rat on D4, D5, D6 and D7 expressed in grams per day are given in table 2 below.

TABLE 2

| Bait consumed | Mean | Standard deviation |
|---|---|---|
| D4 | 17.8 | 5.7 |
| D5 | 16.0 | 4.7 |
| D6 | 14.2 | 4.1 |
| D7 | 9.4 | 3.8 |

It should be noted that no rat consumed a daily amount of bait of less than 1 g/day. All the rats (100%) die between D9 and D10. The mortality is 100% on D10.

The bait containing a low dose of 13.7 ppm of difethialone makes it possible to obtain a mortality rate of 100% while at the same time minimizing the risks of intoxication of animals—especially birds—which prey or carrion-feed on weakened target rodent pests that have consumed a rodenticidal bait according to the invention.

It goes without saying that the invention may be the subject of numerous implementation variants and applications. In particular, a composition, a rodenticidal bait and a process for controlling target rodent pests are subject to an infinite number of variants both in the formulation of the bait and in the embodiments of the process.

The invention claimed is:

1. Laevorotatory enantiomer of a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahyd-ronaphthalene, in which carbons 1 and 3 of the 1,2,3,4-tetrahydronaphthalene group have the same absolute configuration, said laevorotatory enantiomer of said homo-stereoisomer being in isolated form.

2. Composition comprising the laevorotatory enantiomer of a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration with the exclusion of a racemic mixture of laevorotatory and dextrorotatory enantiomers of said homo-stereoisomer of difethialone and wherein the mass amount of the laevorotatory enantiomer of said homo-stereoisomer of difethialone is such that the ratio of this mass amount to the mass amount of difethialone is greater than 95%.

3. Rodenticidal bait comprising a composition at least one excipient that is edible for target rodent pests, and a composition comprising the laevorotatory enantiomer of a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration, with the exclusion of a racemic mixture of laevorotatory and dextrorotatory enantiomers of said homo-stereoisomer of difethialone,
   wherein the mass amount of the laevorotatory enantiomer of said homo-stereoisomer of difethialone is such that the ratio of this mass amount to the mass amount of difethialone is greater than 95%, and wherein the mass amount of difethialone is such that the ratio of this mass amount of difethialone to the mass amount of rodenticidal bait is between 1 ppm and 5 ppm.

4. Bait according to claim 3, wherein the edible excipient comprises at least one food chosen from the group formed from cereal seeds, cereal seed meals, cereal seed flours, cereal seed flakes, cereal bran and non-cereal seeds.

5. Process for controlling target rodent pests, in which there is spread an amount of rodenticidal bait comprising: at least one excipient that is edible for target rodent pests; and a laevorotatory enantiomer of the configurational stereoisomer of difethialone, named homo-stereoisomer, the formula of which is 3-(4'-bromobiphenyl-4-yl)-1-(4-hydroxythiocoumarin-3-yl)-1,2,3,4-tetrahyd-ronaphthalene, in which carbons 1 and 3 of the 1,2,3,4-tetrahydronaphthalene group have the same absolute configuration; with the exclusion of a racemic mixture of the laevorotatory and dextrorotatory enantiomers of said homo-stereoisomer of difethialone, and wherein the mass amount of the laevorotatory enantiomer of said homo-stereoisomer of difethialone is such that the ratio of this mass amount to the mass amount of difethialone is greater than 95%, and wherein the mass amount of difethialone is such that the ratio of this mass amount of difethialone to the mass amount of rodenticidal bait is between 1 ppm and 5 ppm.

6. Process according to claim 5, wherein the following are chosen in combination: the edible excipient; a proportion of laevorotatory enantiomer of said homo-stereoisomer of difethialone relative to said homo-stereoisomer of difethialone; a proportion of laevorotatory enantiomer of said homo-stereoisomer of difethialone relative to the difethialone; a mass proportion of difethialone relative to the rodenticidal bait; and an amount of spread bait; so that target rodent pests consume an amount of difethialone that is sufficient to be lethal to said target rodent pests which consume said bait in the course of a single period of 24 consecutive hours.

7. Process according to claim 5, wherein the following are chosen in combination: the edible excipient; a proportion of laevorotatory enantiomer of said homo-stereoisomer of difethialone relative to said homo-stereoisomer of difethialone; a proportion of laevorotatory enantiomer of said homo-stereoisomer of difethialone relative to the difethialone; a mass proportion of difethialone relative to the rodenticidal bait; and an amount of spread bait; so that target rodent pests consume an amount of difethialone: which is non-lethal to target rodent pests which consume said bait over a period of 24 consecutive hours; and which is sufficient to be lethal to target rodent pests which consume said bait over several 24-hour periods, said periods being consecutive.

8. Chromatographic process for obtaining a laevorotatory enantiomer of a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said homo-stereoisomer have the same absolute configuration, in which process: a high-pressure liquid chromatography column of dimensions 150×2 mm, and comprising a chiral stationary phase constituted of cellulose tris(4-methylbenzoate) particles, said particles having a mean size of 3 pm and having a mean pore size of 1000 Å, is chosen; a mixture formed from acetonitrile (A) and water comprising 0.1% by volume of formic acid (B), with an A/B volume ratio of 80/20 and with a flow rate of the liquid mobile phase in the chromatography column of 0.25 mL/minute, is chosen as liquid mobile phase; separation of the configurational stereoisomers of difethialone is performed at room temperature, during which: a liquid composition comprising said laevorotatory enantiomer of said homo-stereoisomer of difethialone is introduced into the top of the chromatography column; and then the liquid composition is entrained with the mobile phase in the chromatography column under conditions suitable for separating the configurational stereoisomers of difethialone; and a fraction of the mobile phase comprising said laevorotatory enantiomer of said homo-stereoisomer of difethialone is collected with a retention time $t_1$ having a value such that $t_1 < t_2 < t_3 < t_4$; $t_2$, $t_3$ and $t_4$ representing the retention times of each of the configurational stereoisomers of difethialone different from the laevorotatory enantiomer of said homo-stereoisomer of difethialone, separately from a dextrorotatory enantiomer of said homo-stereoisomer of difethialone with a retention time $t_4$ and separately from the laevorotatory and dextrorotatory enantiomers of a configurational stereoisomer of difethialone, named hetero-stereoisomer, in which carbons 1 and 3 of the 1,2,3,4-tetrahydronaphthalene group of said hetero-stereoisomer have different absolute configurations, and of retention times $t_2$ and $t_3$; and then the liquid mobile phase of said fraction is removed so as to obtain said laevorotatory enantiomer of said homo-stereoisomer of difethialone.

* * * * *